United States Patent [19]

Sheehan

[11] Patent Number: 4,526,173

[45] Date of Patent: Jul. 2, 1985

[54] SKIN CLOSURE DEVICE

[75] Inventor: Joseph C. M. Sheehan, Burr Ridge, Ill.

[73] Assignee: Kells Medical, Inc., Burr Ridge, Ill.

[21] Appl. No.: 472,053

[22] Filed: Mar. 10, 1983

Related U.S. Application Data

[63] Continuation-in-part of Ser. No. 367,671, Apr. 12, 1982, abandoned.

[51] Int. Cl.³ .............................................. A61B 17/08
[52] U.S. Cl. ................................................. 128/335
[58] Field of Search .................. 128/334 R, 335, 337, 128/325–326, 346; 227/DIG. 1 B

[56] References Cited

U.S. PATENT DOCUMENTS

| | | | |
|---|---|---|---|
| 655,190 | 8/1900 | Bramson | 128/335 |
| 1,452,372 | 10/1921 | Gomez. | |
| 3,648,705 | 3/1972 | Lary | 128/335 |
| 3,695,271 | 10/1972 | Chodorow | 128/335 |
| 3,825,010 | 7/1974 | McDonald. | |
| 3,863,640 | 2/1975 | Hauerstock. | |
| 3,983,878 | 10/1976 | Kawchitch | 128/335 |
| 4,275,813 | 6/1981 | Noiles. | |

Primary Examiner—Stephen C. Pellegrino
Assistant Examiner—Gene B. Kartchner
Attorney, Agent, or Firm—Willian Brinks Olds Hofer Gilson & Lione Ltd.

[57] ABSTRACT

An improved skin closure device is disclosed which includes a pair of parallel members adapted to be positioned along either side of a wound to be closed. The device includes a plurality of pins associated with the parallel members for the purpose of urging the dermis on either side of the wound together, and an adhesive interface adapted to maintain the members in a firmly positioned orientation with respect to the epidermis in order to hold the epidermis on either side of the wound together. Some embodiments of the skin closure device of this invention include a housing adapted to lock the parallel members in place with respect to each other.

36 Claims, 28 Drawing Figures

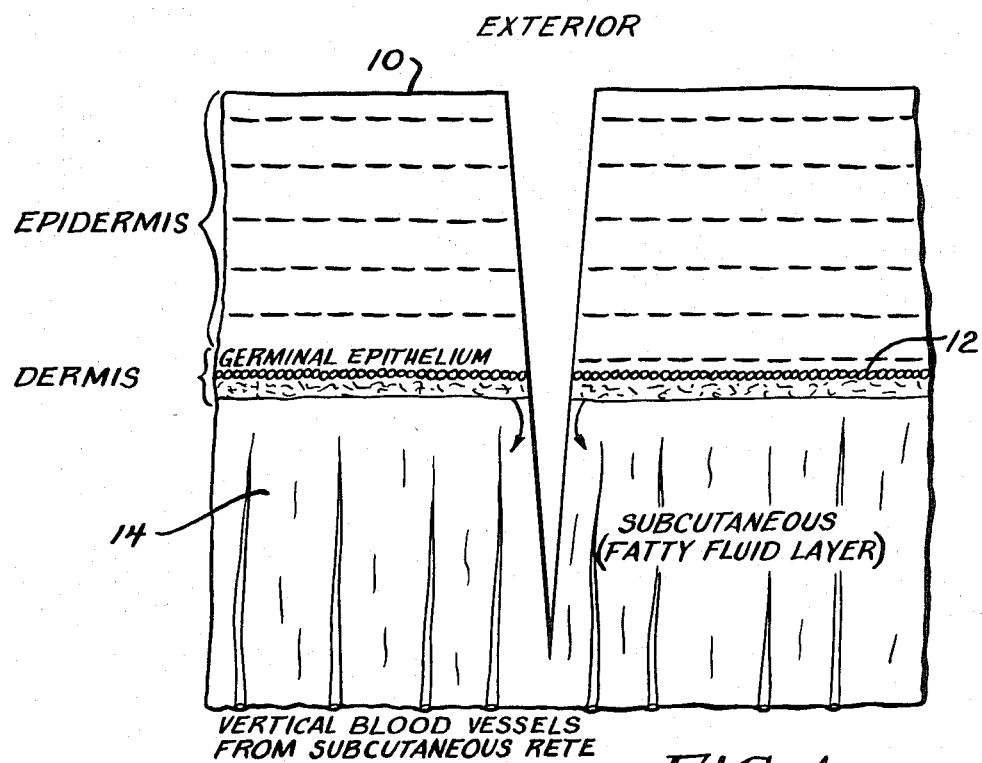
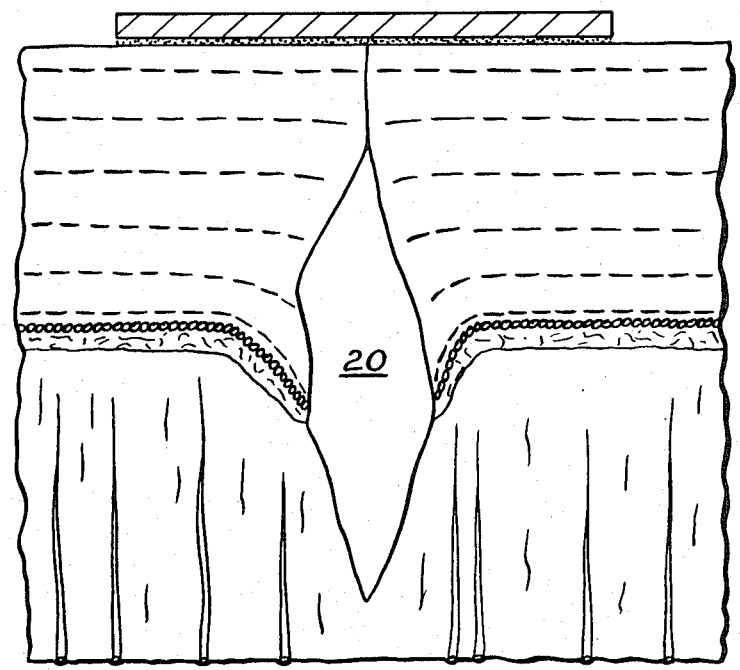

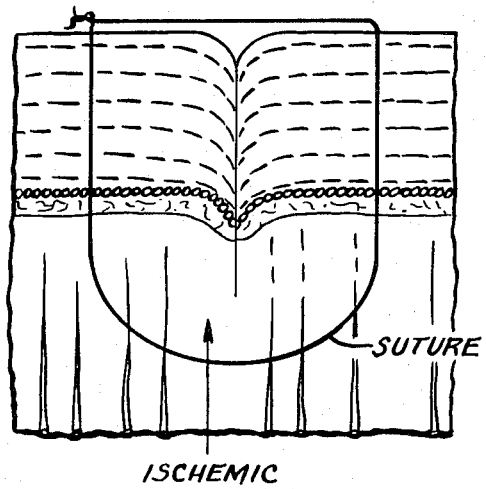
FIG. 3 — ISCHEMIC — SUTURE
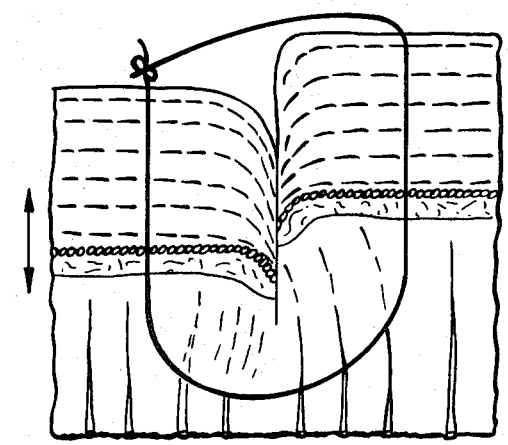
FIG. 3a — VERTICAL SHIFT
FIG. 4
UNEQUAL CENTERING OF STAPLE
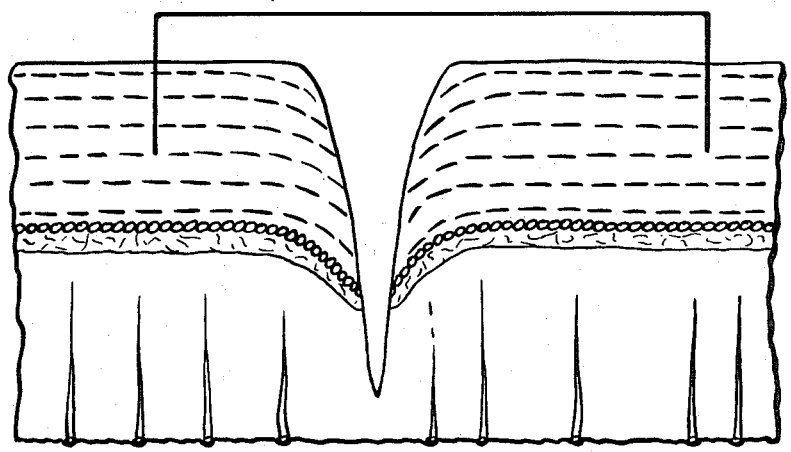
FIG. 4a
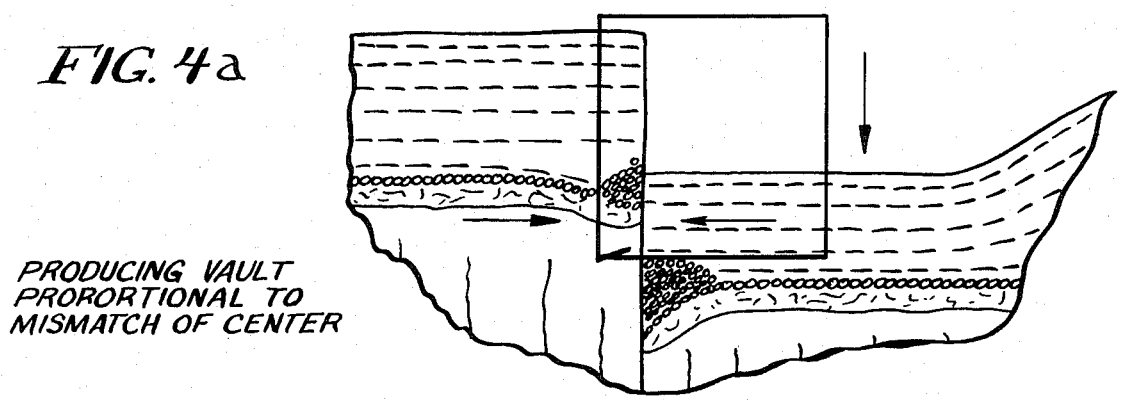
PRODUCING VAULT PROPORTIONAL TO MISMATCH OF CENTER

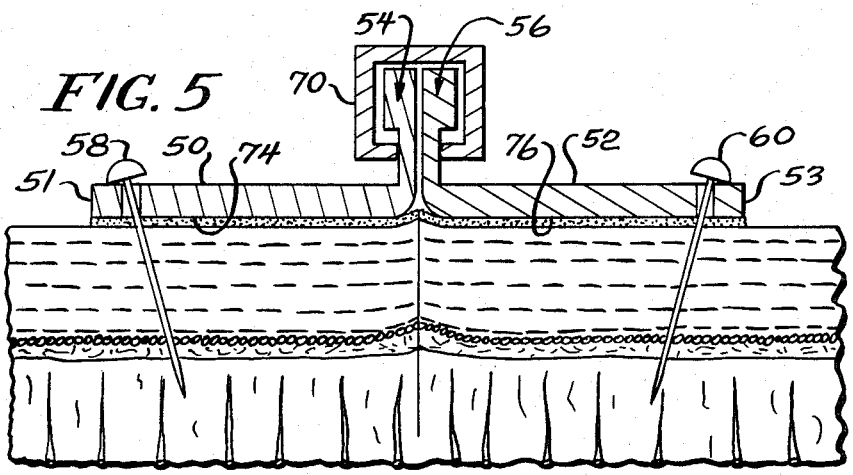
FIG. 5
FIG. 5a
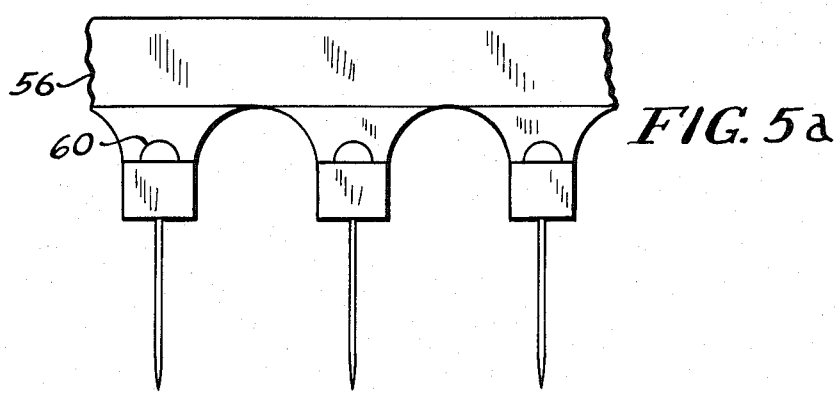
FIG. 6
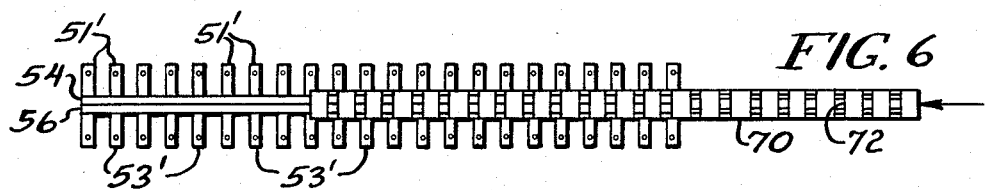
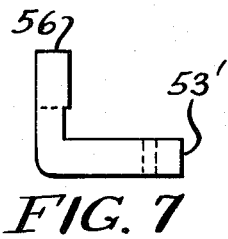
FIG. 7
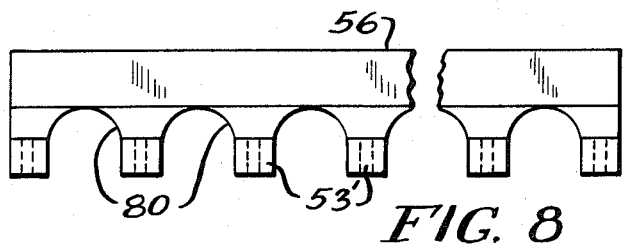
FIG. 8
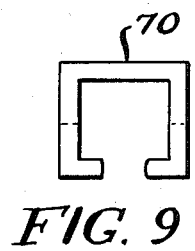
FIG. 9
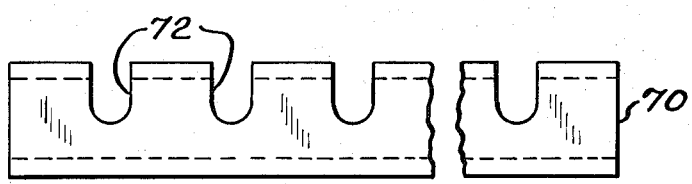
FIG. 9a

SKIN CLOSURE DEVICE

IDENTIFICATION OF RELATED APPLICATION

This application is a continuation-in-part of copending application Ser. No. 367,671, filed Apr. 12, 1982 now abandoned.

FIELD OF THE INVENTION

The present invention relates to an improved skin closure device in the nature of a surgical appliance which is particularly adapted for use in the closure of skin wounds, whether created surgically or by trauma, which device is adapted to hold the wound in a closed position to facilitate the healing process and to minimize the generation and residue of scar tissue.

BACKGROUND OF THE INVENTION

Conventional surgical practice involves the closure of skin wounds with the use of sutures, clamps, adhesive materials or other similar means.

It is well recognized that skin wounds, whether created by trauma or as a result of surgery, should be closed as soon as possible to avoid contamination and infection, and to minimize the development of scar tissue. The deliberate creation of skin wounds by surgery conventionally requires closure of the wound immediately following the surgery to avoid contamination of the wound and to facilitate repair of the tissue so that the patient may be returned to his normal environment.

Simple suturing of the skin has persisted as a dominant method of skin closure at the present time under a wide range of circumstances. The speed of surgery, however, has developed as an important facet of medical procedure and faster methods for skin closure have been developed, including the use of staples as an accepted method.

In an effort to provide rapid skin closure, a variety of alternatives to sutures and staples have been developed. For example, the following patents disclose various types of brackets which are adhesively affixed to the skin adjacent a wound and are then releasably secured together to close the wound: U.S. Pat. Nos. 4,114,624, 3,933,158, 3,863,640 to Haverstock; U.S. Pat. No. 3,516,909 to Howell; Australian Pat. No. 477,704 to Kawchitch; and West German Pat. No. 2,038,038 to Keil. In addition, the following patents disclose various types of brackets which are affixed to the skin by pins adjacent a wound and are then releasably secured together to close the wound: U.S. Pat. No. 3,825,010 to McDonald and U.S. Pat. No. 4,073,298 to LeRoy. U.S. Pat. No. 1,452,372 to Gomez discloses a skin closure device of the general type discussed above in which both adhesives and pins are used to secure the brackets to the skin.

At the present time, under normal circumstances, there are three generally recognized methods of skin closure. One involves a simple bandaging of the skin with an adhesive material which involves pulling the skin edges together from edge-to-edge with adhesive straps. Another method involves the suturing of wounds through use of a variety of skin suture methods. The third involves skin closure by stapling the skin edges together. In addition, a fourth approach is to use one of the separable brackets discussed above, though the majority of these brackets have not achieved widespread acceptance.

The skin closure devices set forth herein provide significant improvements over the skin closure devices discussed above.

ANATOMY OF THE SKIN

In general, human skin is made up of many separately defined layers, which for simplicity can be grouped in three commonly defined layers. The outer layer is called the epidermis and includes a layer of dead cells which gradually form a pavement network, layer upon layer. This network forms an impermeable boundary of dead or dying cells at the exterior or superficial layer of the skin. These cells are gradually replaced in a continually evolving process as new layers of cells are produced from within.

The second layer to be discussed here is the germinal epithelium, sometimes called the dermis, which is the true growth area of the skin. The germinal epithelium is a relatively thin layer in relation to the other two layers being generally described here. This basement, or germinal epithelium, is constantly replacing the layer above it and gradually pushing the most superficial layer towards the outside of the skin. The proper joining of this layer is important since this is the layer which, when joined properly end-to-end with a surgical closure device, will give a good or near perfect junction between the dermis on one side of the wound and the dermis of the other side, thereby minimizing the formation of scar tissue. For example, this is the layer which, when burned by deep burns, will often require skin graft. In general, nothing can replace this layer of skin other than germinal epithelium itself, either growing from the side or transplanted when lost.

Beneath the germinal epithelium lies the basement membrane, which is a thin layer of delicate non-cellular material of a fine filamentous texture whose principal component is collagen. This layer gives body and support to the overlying germinal epithelium, and is a fatty, fluid-like layer which provides a generally defined cushioning effect whereby the germinal epithelium can easily slide over the muscles. This subcutaneous tissue has poor adherent qualities and poor healing qualities, of itself, since it is of a semi-fluid character in the normal state and often does not come together well when sutured.

The nature and physical properties of each of the three skin layers generally described above are somewhat different. For example, the outer, crusty layer of stratified epithelium, described as the epidermis, is relatively dehydrated. It generally varies in thickness with the maximum thickness being on the sole of the foot and the minimum thickness being in the facial area. It has the ability to be pulled together and can be joined with an adhesive material to close a wound in the stratified epithelium.

It should be noted, however, that the germinal epithelium and the basement membrane, generally described above, lie at some depth with respect to the epidermis and are critically important to skin closure since they are the primary source of healing with respect to any skin wound.

The basement membrane is made up of high density collagen material which, when cut, has a tendency to recoil and, subsequently, will often result in movement inwards toward the body of the germinal epithelium. The fatty layer beneath offers insufficient resistance to prevent this recoil mechanism and may allow the germinal epithelium to be maintained in a retracted condition over the course of a significant period of time.

SUMMARY OF THE INVENTION

The present invention is directed to improved skin closure devices which to a large extent overcome the problems inherent in the use of sutures, adhesives or stapling means for skin closure, which provide an environment for rapid healing of the wound, and which minimize the development of scar tissue.

According to this invention, a closure device for a skin wound is provided which includes adhesive means for adhesively bonding exterior surfaces of the epidermis at points closely adjacent the two marginal edges of the wound, and pin means for mechanically engaging an internal skin layer (such as the dermis) on both sides of the wound near the marginal edges of the wound. Means are provided for positioning the adhesive means to hold the epidermis on the two sides of the wound together in alignment and for simultaneously positioning the pin means to hold the internal skin layer on the two sides of the wound together in alignment in order to promote rapid healing of the wound and to minimize the formation of scar tissue.

In the preferred embodiments discussed below, the pin means can take the form of pins slidably mounted in pin harnesses or staples, and the adhesive means can take the form of adhesive coatings on pin harnesses or adhesive layers positioned between the bridge of a staple and the wound. Further aspects of this invention related to the geometry and function of specific wound closure devices are set out in detail in the following detailed description.

The skin closure devices disclosed and claimed herein provide important advantages in that they provide close positioning and proper alignment of both the basement membrane and the epidermis of the skin. Such alignment of both exterior and internal skin layers results in a reduction of the production of scar tissue and in the development of a more cosmetically acceptable wound after healing. Also, certain embodiments of the present invention provide means for rapidly closing a wound, which in surgical procedures results in a decrease in operating time and exposure of patients to anesthetic risk conditions. In addition, certain preferred embodiments of this invention create an environment for the reduction of bacterial contamination.

The invention itself, together with further objects and attendant advantages, will best be understood by reference to the following detailed description taken in conjunction with the accompanying drawings.

BRIEF DESCRIPTION OF THE DRAWINGS

FIG. 1 is a schematic representation of skin tissue defining a wound therein which may be closed by devices of the type disclosed herein.

FIG. 2 is a schematic representation of a prior art skin closure device involving the use of an adhesive material.

FIG. 3 is a schematic representation of a prior art skin closure means involving the use of a suture.

FIG. 3a is a schematic representation of a vertical shift of tissue with a prior art suture closure.

FIG. 4 is a schematic representation of a prior art staple closure for a skin wound.

FIG. 4a is a schematic representation of a vertical shift of tissue as a result of off-center orientation of the staple of FIG. 4 in closure.

FIG. 5 is a cross sectional elevation of a first preferred embodiment of the skin closure device of the present invention.

FIG. 5a is a partial side elevation of the device of FIG. 5.

FIG. 6 is a top plan view of the device of FIG. 5 showing the lateral plate assembly and closure housing in partially assembled relation.

FIG. 7 is an end view of the one of the lateral plate elements of the assembly of FIG. 5.

FIG. 8 is a segmented side view of the plate element of FIG. 7.

FIG. 9 is an end view of the closure housing included in the assembly of FIG. 6.

FIG. 9a is a segmented side elevation of the housing of FIG. 9.

DETAILED DESCRIPTION OF THE PRESENTLY PREFERRED EMBODIMENTS

Figure 10:
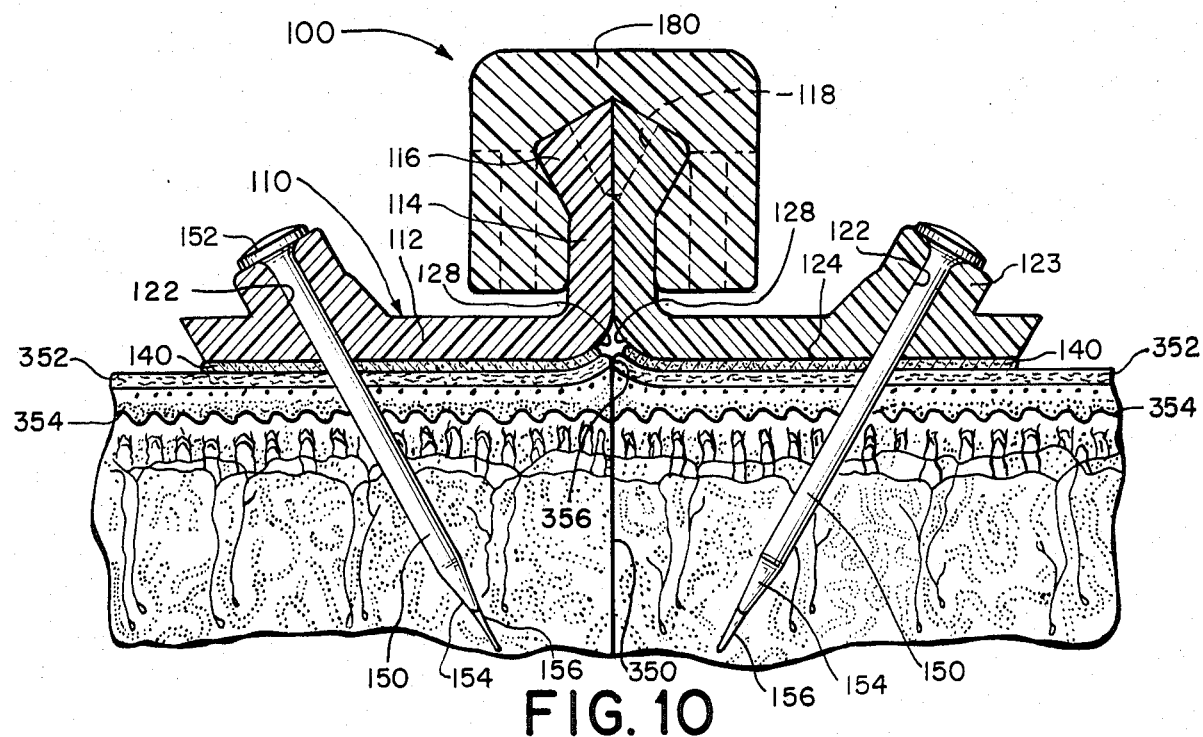
FIG. 10 is a cross sectional elevational view of a second preferred embodiment of the skin closure device of the present invention.

Referring specifically to FIG. 1 of the drawings, it should be noted that this drawing is a schematic representation of the skin, which, as described above, is made up of many layers. For simplification, these layers can be grouped into three layers with the outer layer being called the epidermis as indicated at 10 in FIG. 1. As noted above, the epidermis 10 defines the outer skin layer and forms an impermeable boundary made up of a network of dying or dead cells.

The basement, or germinal epithelium 12 defines the cell growth area where the growth of cells by multiplication and division replaces the layer above it and gradually pushes the most superficial layer towards the outside of the skin. This germinal epithelium 12 is called the dermis and is the true growth area of the skin. This, it should be noted, is one of the main skin layers involved in the healing process, since this is the layer which, when joined properly in an end-to-end relationship, will provide for optimal healing conditions and for minimal development of scar tissue.

The skin layer lying beneath the germinal epithelium or dermis 12 is the basement membrane 14 which, as noted above, is a thin layer of delicate non-cellular material of a fine filamentous texture whose principal component is collagen. The subcutaneous tissue is fatty and fluid-like and gives a cushioning effect so that the dermis 12 can slide easily over the muscles. It should be noted that this subcutaneous tissue has a poor adherent quality, or poor healing quality, since it is in a semi-fluid condition in its normal state and generally does not come together well when sutured.

Referring now to FIG. 2 of the drawings, this figure shows an illustrative example of one of three common methods of skin closure of the prior art, notably, closure of a skin wound with an adhesive material. With reference to the foregoing description of the various layers of dermis, epidermis and subcutaneous tissue, it can be seen that an adhesive layer of the type shown in FIG. 2 brings only the outer border of the epidermis together. In many cases this type of skin closure device does not bring the deep layer of the dermis together, in view of the fact that this device does not come into contact with the dermis in any physical manner. Accordingly, an adhesive skin closure device serves primarily as a dressing to prevent bacterial contamination but does not completely control the recoil of the dermis which can result in the creation of a space, or void. Such a void usually is filled by a hemorrhage clot or some serous clot of seepage of the normal tissue fluids into this area as seen at 20 of FIG. 2. Such a clot 20 will in general eventually coagulate to define a stiffened network across which the dermis eventually will grow in an irregular manner until the dermis is complete. However, such a growth pattern of the dermis often results in a skin irregular underlying basement membrane and an inherent defect which will sometimes persist as an irregularity for the remainder of the life of the patient. It can readily be seen that the use of an adhesive closure, by itself, may result in significant cosmetic problems related to the formation of a permanent, undesirable scar.

Another prior art method of wound closure, schematically represented in FIG. 3, is the suture means of closure. It should be recognized that there are many forms of sutures and suture materials available for the closure of wounds. It is recognized that it is often preferable to use a non-reactive material rather than an absorbable material for sutures, since absorbable sutures will often produce a tissue reaction around the suture, giving rise to scar formation to an extent greater than that which may be cosmetically acceptable to a patient.

Suturing generally is more acceptable in certain areas, such as in the facial area, where the epidermis is of a minimum thickness. Under these circumstances, the suture line on the superficial surface of the skin tends to keep the skin aligned in generally parallel layers, thereby closing the dead space beneath the epidermis to bring the recoiled edges of the dermis into a closely aligned relationship. Such a closure generally will give an acceptable scar tissue for cosmetic purposes. However, such a closure is to some extent unpredictable and to some extent the quality of the closure depends upon the depth of the epidermis. In general, the thinner the epidermis, the greater the probability of getting the dermis properly aligned. A greater depth of tissue can make it difficult to achieve proper alignment, and consequent misalignment of the dermis can result in the development of unacceptable scar tissue. That is, a vertical shift of one layer of epidermis with respect to the other in a "step" fashion (as shown, for example, in FIG. 3a), will result in misalignment of the basement membranes which can eventually result in a widened scar tissue that generally is cosmetically undesirable.

A third commonly employed prior art method for closure of a wound involves the use of staples (as in FIG. 4). This closure method involves little improvement in the avoidance of scar tissue formation, and stapling can be a less predictable means for closure of a wound since every staple is individually inserted into the skin.

Generally, the skin is held everted as the staple is applied across the wound edge, and the staple, when inserted, compresses the wound with the hope that the everted edges will provide the desired alignment. This is a relatively imprecise method of obtaining the desired alignment of the basement membrane of the skin since there is little control over the membrane itself during the closure procedure. As a result, there is a significant chance of misalignment, and a resulting vertical shift can result in a less satisfactory wound closure than the simple suture. FIG. 4a illustrates such a vertical shift.

Staples of the type shown in FIG. 4 provide the advantage that they substantially speed the time of closure. In some instances, staples are preferable to simple suturing where the speed of surgery is an element in treatment of the patient. It should be noted, however, that unless the staple is properly placed in the center of the wound upon closure, a vertical defect is often created which is greater when the staple is placed more off-center with respect to the wound. (See FIGS. 4 and 4a).

THE FIRST PREFERRED EMBODIMENT

Turning now to FIGS. 5-9a, FIG. 5 is a schematic representation, in section, of a first preferred embodiment of this invention. This embodiment is a skin closure device which, to a large extent, overcomes problems inherent in the use of adhesive, suturing or stapling means for skin closure. This embodiment provides a more exacting method of skin closure which minimizes the time needed to close a wound as well as the formation of scar tissue.

It should be noted that an important advantage of the skin closure device of FIGS. 5-9a is that it allows the basement membrane of the skin to be aligned properly. This is a significant factor in the reduction of the production of scar tissue and results in a more cosmetically acceptable wound closure.

The speed of a wound closure is an important factor, since in many instances decreased operating time is highly desirable to reduce the anesthetic risk and to reduce the incidence of bacterial contamination which might occur in a prolonged operation. The improved closure device of FIGS. 5-9a provides the further important advantage of extremely rapid skin closure.

Another desirable feature of the embodiment of FIGS. 5-9a is its versatility in that this embodiment allows the transfixing pins to be removed individually at the surgeon's discretion without the removal of the entire apparatus. This approach leaves the apparatus intact while still allowing for the early removal of pins as may be appropriate and indicated in certain rapidly healing areas such as the face, head and neck.

The device shown in FIGS. 5–9a overcomes to a large extent the problems discussed above through the use of laterally extending plates which are anchored with respect to the wound through a combination of pins extending along the outside edges of said plates and an adhesive which secures the plates to the epidermis and isolates the pins with respect to the skin to avoid movement of the pins which could give rise to tissue damage.

The pins utilized in the embodiment of FIGS. 5–9a may be formed of stainless steel, chrome, cobalt or titanium alloys, or some other suitable non-reactive rigid material.

The ease of application of the present device with respect to the wound permits its use in a wide range of elective surgical procedures without the need to change traditional methods of skin and wound preparation.

For example, when used in a surgical procedure, the closure device of FIGS. 5–9a may first be placed so that the inner abutting portions of the laterally spaced plates extend along the area to be incised. The closure housing is then removed from the device and the incision then may be made in the region defined between the abutting inner plate portions. It can readily be seen that accurate re-alignment of the incised tissue can quickly be realized by bringing the plates back together in an abutting relation and placing the closure housing over the upstanding legs of the plates to hold the plates in assembled relation as schematically represented in FIG. 5 of the drawings.

To obtain proper wound healing, it is important to bring the epidermis, the dermis, as well as the outer layers of the subcutaneous tissue into close apposition and to maintain this orientation during the healing process. This maintenance of orientation is easily obtained with the apparatus of FIGS. 5–9a, and a skin wound can be closed extremely rapidly.

Preferably, all of the materials employed in the making of the device of FIGS. 5–9a are non-reactive with respect to human tissue and, subsequently, minimum scar formation will result from the use of this device.

The apparatus of FIGS. 5–9a includes a pair of spaced apart plate elements 50 and 52. Each of these plate elements includes a plurality of horizontally extending legs shown at 51 and 53 in FIG. 5, each extending laterally into a respective upstanding leg element 54 and 56.

The general configuration of the plates may readily be seen in FIGS. 6, 7 and 8. The legs 51 and 53 are shaped as a series of spaced apart, projecting, finger-like elements 51 and 53 extending in spaced apart relation along the length of the plate sections.

Each of the spaced apart finger-like elements 51 and 53 of the plates 50 and 52, respectively, is provided with a pin as shown at 58 and 60, extending through the outer terminal portion of the finger-like elements.

It should be noted that various wound closures may require different closure forces and it may not be necessary to include a pin at the outer terminal portion of each finger-like element. For purposes of illustration the pins are included at said outer terminal portions in FIGS. 5, 5a and 6.

The skin penetration portion of the pins is provided with a beveled terminal portion for the purposes to be noted hereinbelow.

The upstanding portions 54 and 56 of the plates 50 and 52, respectively, include an enlarged portion at the upper terminals thereof to cooperatively associate with a closure housing 70 which will hold the upstanding portions 54 and 56 of the plates 50 and 52 in abutting relation. The housing 70, therefore, will serve to hold the entire closure device in fully assembled configuration to accomplish wound closure in association with the holding forces of the pins, which extend into the tissue, and an adhesive, which bonds the plates 50, 52 to the epidermis. It also should be noted that the housing 70 holds the assembled structure in a fixed orientation to avoid vertical misalignment of the plates 50 and 52 in use.

The adhesive layer is provided along the bottom portions 74 and 76 of the laterally extending portions of the legs of the plates 50 and 52. This adhesive layer is applied to the bottom surface of the plates of the apparatus to maintain the plates in a firmly anchored orientation with respect to the epidermis. The adhesive layer controls any lateral motion of the epidermis and it secures the apparatus to the epidermis, thereby bringing the epidermis in a desired, edge-to-edge, closed configuration.

The laterally extending legs of the plates, as defined by the spaced apart finger-like elements, are made sufficiently wide to spread the distribution of closure forces over a wide area, thereby reducing scar formation which otherwise might have occurred with the use of a stitch, suture or staple that might lie on the skin for a prolonged period. It generally is recognized that the healing process may take anywhere from ten to fourteen days. Sutures or staples which remain in contact with the skin during this process can give rise to skin irritation.

The pins 58 and 60 are preferably provided with a knife-like edge to allow the pins to cut the skin during insertion. This cutting action is preferable to the press fitting action characteristic of use of a regular safety pin, or the like. The sharpened edge of the pins 58, 60 is preferably provided with an acute angle of at least 60 degrees which produces a sharp linear cut in the skin upon insertion of the pin. In this way, scar production by the pins 58, 60 is minimized. This knife-like cutting edge on the pins 58, 60 provides significant advantages.

The pins 58 and 60 may be formed such that they extend slightly inwardly toward the central part of the device as shown in FIG. 5 to provide enhanced wound closure forces. This inward pitch may preferably be on the order of about 15 degrees.

The pins are preferably formed of a high-grade stainless surgical steel which is non-reactive to the body and which will produce no significant soft tissue reaction around it which might be detrimental in the production of scar tissue.

The laterally extending plates 51 and 53, which in the embodiment of FIGS. 5–9a are defined by spaced apart finger-like elements, are integrally attached to the upstanding legs 54 and 56, respectively. The inward portions of the plates 51 and 53 at the portion of attachment to the upstanding legs 54 and 56, respectively, define a radius of curvature which is provided to allow the skin to be everted during the healing process. This eversion of the skin is highly controlled by the shape of the curve joining the laterally extending and upstanding leg portions of the plates 50 and 52 and permits a slight movement of the inboard portion of the plates in relation to the wound being controlled by the assembly. This action in cooperation with the action of the pins 58, 60 controls, via the vertex of the wound, the deeper dermis and tends to neutralize the inversion effect or recoil of the basement membrane during the healing process. The result is that a straight epithilial membrane is defined in end-to-end relationship which often will produce almost no void or vertical step in the depths of the wound.

The closure housing 70, when in place, locks the two plate elements 50 and 52 in assembled relation and prevents overriding or vertical motion of one side of the wound with respect to other, thereby maintaining proper alignment of the closure. The housing member 70 may be serrated as shown in FIG. 9a of the drawings with the serrations being defined by the cutout sections 72 spaced therealong to provide for flexibility of the assembled apparatus and to allow for free drainage from between the upstanding legs of the plates. In use, the closure housing 70 is positioned in place over the upstanding legs 54 and 56 to define means for rapid approximation of each skin edge being controlled by the apparatus, whether the apparatus is applied after the wound was created or the apparatus is applied prior to the incision of the wound.

The pins 58, 60 are individually pushed into the skin through the pre-formed openings of the finger elements of the plates. A multiple pin insertion apparatus can be provided for this purpose which requires a minimum amount of force to be exerted at the skin edge upon insertion of the pins. It should be noted that, in the preferred embodiment of FIGS. 5–9a, the pins have not been incorporated or molded into the apparatus. This allows the surgeon to remove the pins individually or in groups in accordance with defined surgical procedures. The pins are provided with a safety head on them to prevent migration of the pin into the depth of the wound and also to allow for easy removal of the pin with a simple forceps action, thereby leaving the plate adherent to the skin to maintain the wound in an essentially controlled manner once the serous clot and early epithelization has occurred but before full strength has been obtained.

It should be noted that in the preferred embodiment of FIGS. 5–9a suitable drainage sites are provided via the recessed portions 80 (FIG. 8) extending in spaced apart relation along the base of the conjunction of the laterally extending legs 51 and 53 and upstanding leg portions 54 and 56. These drainage sites 80 allow for free drainage to occur from the wound and for the removal laterally of the wound of any excess serous secretion that may build up at the wound edges or to accommodate any hematoma that may build up and tend to lift the apparatus which would subsequently result in discharge of material from the drainage sites 80.

It also should be noted that the drainage sites allow for easy examination of the wound edges to insure that the wound has been carefully brought in apposition and has not been left excessively everted or distracted by the application of the apparatus.

It should be noted that blood is supplied to the skin via a reticular network which is a vertically oriented system. The apparatus of FIGS. 5–9a, unlike sutures or the like, does not interfere or put under compression the skin edges and allows for normal post-operative swelling to occur and recede without interfering with the blood supply to the vital healing tissue. This is an important aspect of the embodiment of FIGS. 5–9a and is a characteristic of the design and use of this apparatus in assembled relation in holding the wound in a closed orientation during the healing process.

It can readily be seen that the laterally extending plate elements 50 and 52 and the closure means may be of any desired length and are made of material which may readily be cut with any convenient apparatus to the exact length desired by the physician or surgeon.

In one preferred embodiment of the device of FIGS. 5–9a, the plates and closure housing are made of nylon which in its characteristic form will have sufficient flexibility in use, so that the apparatus may be placed in a lateral spaced apart configuration with respect to the wound in any desired configuration and made to adapt the characteristic nature of the wound. This flexibility characteristic is, of course, enhanced in the preferred embodiment of FIGS. 5–9a by the use of the spaced apart finger-like projections on the laterally extending plate elements 51 and 53 and the drainage site serrations 80 associated therewith. The removal of this material, of course, permits increased flexibility of the apparatus for convenience in use. It should be noted, however, that a material which is too flexible may defeat the purpose of the apparatus if the material is not sufficiently rigid to maintain the wound closure in proper orientation. Therefore, it is important to provide the degree with a proper degree of flexibility which permits a preferred orientation of the device with respect to the wound while still being sufficiently rigid to hold the wound in the desired closed orientation during the healing process.

During the application procedure it should be noted that the pins are in a fully retracted position and do not extend substantially below the lower face of the laterally extending segments 51 and 53. This permits initial application in the non-penetrating area of the skin without the need for holding the skin edges with a forceps and further traumatizing the delicate skin edges. It should be noted that the undersides of the laterally extending plate elements 51 and 53 are provided with the adhesive interface which will orient the plate elements with respect to the skin. Accordingly, the apparatus can be put on atraumatically and closed without any forceps touching the skin edge. Further, the adhesive layer on the underside of the laterally extending plate elements is such that if the element is applied in an unsatisfactory orientation it can easily be removed and reapplied in the proper orientation of the plate elements 50 and 52 with respect to the wound. The pins may be inserted individually or in groups to provide a rapid rate of closure which is substantially in excess of commonly used suturing techniques and which may even be faster than the application of staples for wound closure. Since there is substantially no motion between the pins which transfix the skin and the surrounding skin (a feature provided by the adhesive interface associated with the plate), there is substantially no motion of the skin at the site of the pins. The adhesive interface closes the skin puncture at the pin to bacterial contamination over the course of the healing process and also reduces the motion of the pins which could result in the production of scar tissue. It has been my experience that this combination of pins and adhesive along with the sharp pin knife edge produces an atraumatic and almost scarless pin site.

The apparatus of FIGS. 5–9a can be applied either after the wound has been created at the time of surgery or before the skin is cut and then subsequently separated at the time of the surgical incision. This latter approach minimizes the time required to close the wound. It also should be noted that the removal of the apparatus from the skin can occur in two ways: the pins can be removed one at a time at the time of healing, or alternately one edge of the apparatus can be lifted and peeled off. There is little pain involved in this maneuver since the pins are typically in place for a period of more than forty-eight hours, and removal of the pins in such a manner will typically not cause patient discomfort. Patient discomfort in the removal of sutures or staples can be greater since staples tend to catch the patient on the deep elbow as they are removed.

ALTERNATIVE PREFERRED EMBODIMENTS

Turning now to FIGS. 10 through 24, a number of alternative embodiments of the present invention will be discussed in detail. In these drawings, FIGS. 10 through 19 disclose a second preferred embodiment of this invention which is in many ways similar to the first preferred embodiment described above. FIGS. 20 through 24 disclose three additional embodiments which differ significantly from the first two embodiments in important respects. In FIGS. 10 and 21–24, the reference numeral 350 has been used to designate a skin wound, the reference numeral 352 has been used to designate superficial skin layers (the epidermis), the reference numeral 354 has been used to designate the dermis, and reference numeral 356 has been used to designate the marginal edge of the skin wound.

Figure 11:
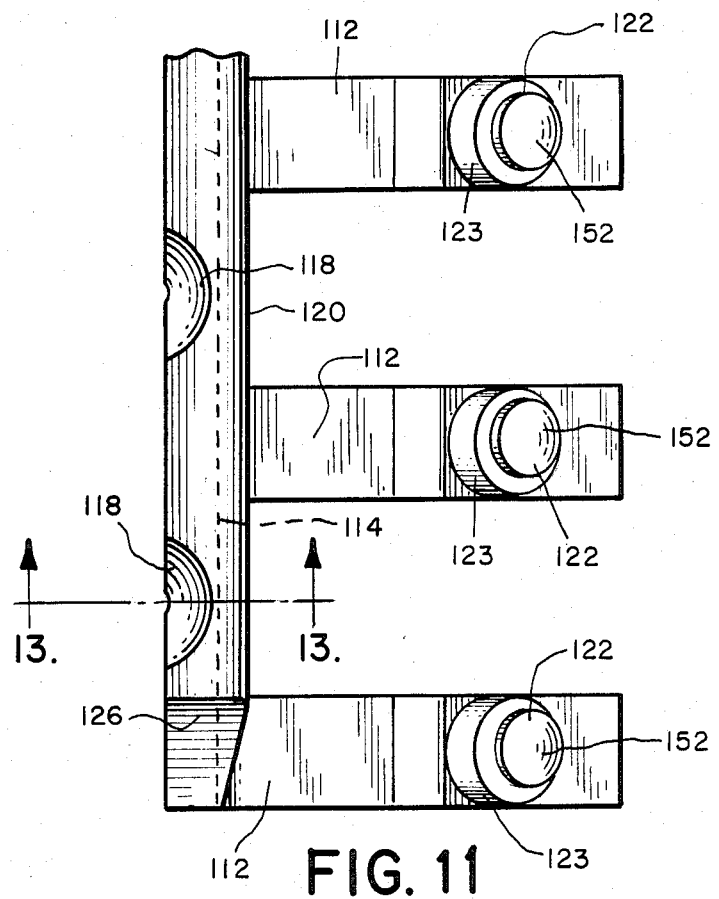
FIG. 11 is a top plan view of a portion of one of the pin harnesses of the embodiment of FIG. 10.
Figure 12:
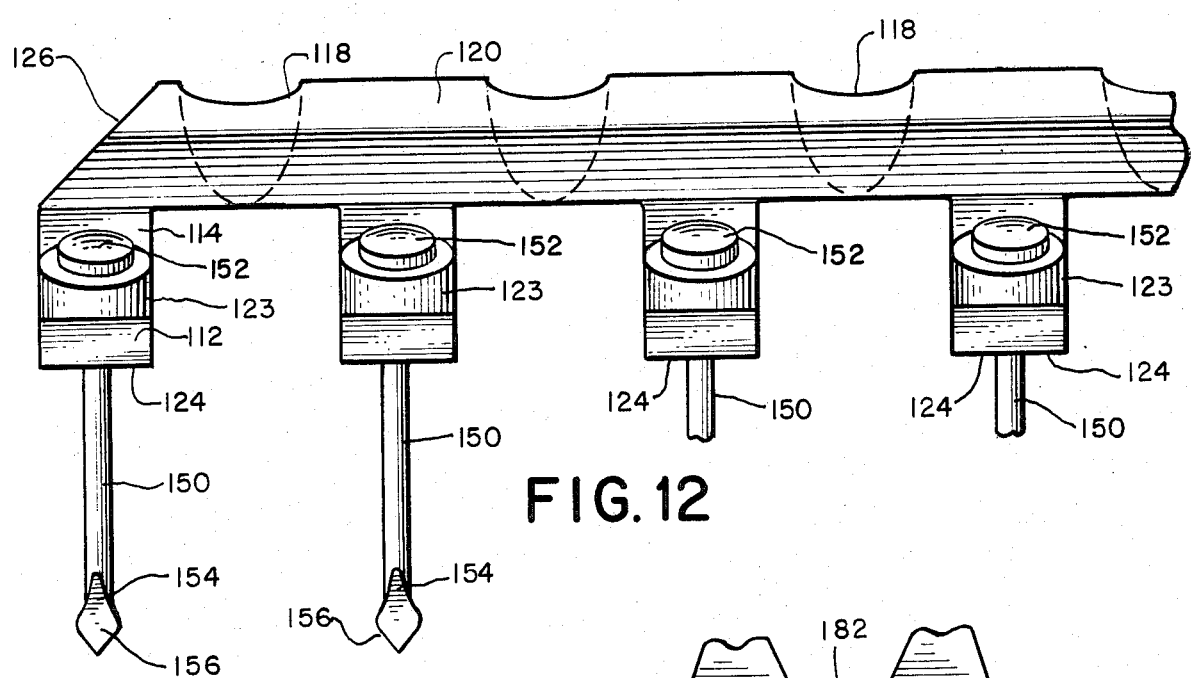
FIG. 12 is a side elevational view of a portion of the pin harness of FIG. 10.
Figure 13:
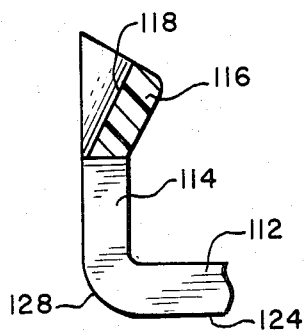
FIG. 13 is a sectional view taken along line 13—13 of FIG. 11.

Turning now to FIGS. 10 through 19, a second preferred embodiment on the skin closure device of this invention is there illustrated. This second preferred embodiment 100 includes two pin harnesses 110. The relationship between these two pin harnesses 110 in the assembled configuration is shown in FIG. 10. FIGS. 11 through 13 show various additional views of one of the pin harnesses 110 in order further to define its structure. As shown in these figures, each of the pin harnesses 110 includes an array of skin contacting members 112. Each of these skin contacting members 112 is shaped as an elongated, finger-like projection which is mounted to a respective upright member 114. Each of the upright members is in turn mounted to a longitudinal rail 116 which extends across the plurality of the skin contacting members 112. The members 112, 114 and the rail 116 cooperate to form a plurality of apertures 120 therebetween. As best shown in FIG. 12, the rail 116 is maintained above the level of the skin, and the apertures 120 allow free drainage of fluids from the skin wound. In addition, the rail 116 defines a spaced plurality of recesses 118 which serve further to enhance drainage from the skin wound. As best shown in FIG. 12, each end 126 of each of the rails 116 is preferably beveled to facilitate assembly of the skin closure device. Each of the skin contacting members 112 defines a respective pin guide 122 which terminates at its upper end in a boss 123. As best shown in FIG. 10, each of the skin contacting members 112 defines a respective skin contacting surface 124 along its underside surface. The innermost surface of each of the skin contacting members 112 is provided with a radius of curvature 128 to allow for skin eversion adjacent the skin wound.

In this preferred embodiment, the pin guides 122 are spaced such that five pin guides 122 are provided per inch on each pin harness 110. A preferred range for the pin guide spacing is between 3 and 8 pin guides 122 per inch. Simply by way of illustration and not by way of limitation, each of the radiused portions 128 is in this preferred embodiment provided with a radius of curvature of 0.035 inches. Preferably, the pin guides 122 are sized to receive the respective pins in a sliding fit so as to orient the pins properly for penetration of the skin. The angle of the pin guides with respect to the perpendicular to the skin surface can vary within the range of about 0 degrees to about 35 degrees. Within this range, the preferred angle of the pin guides 122 with respect to the perpendicular is about 15 degrees to about 30 degrees. In the presently preferred embodiment, a pin guide angle of about 20 degrees with respect to the perpendicular is considered optimum.

Each of the skin contacting surfaces 124 of the pin harnesses 110 is provided with an adhesive layer 140. Preferably, this adhesive layer 140 extends both around the lower portion of the pin guides 122 as well as to a point partially up the radiused portions 128. Preferably, this adhesive layer is precoated onto the skin contacting surfaces 124 during manufacture.

A wide variety of skin adhesives are suitable for use with the present invention. However, in the presently preferred embodiment the adhesive layer 140 is formed of a skin adhesive distributed by Dow Corning as Adhesive No. 355. This adhesive is a solution of 18.5 percent by weight of dimethylpolysiloxane in trichlorotrifluorethane (Freon). Of course, this example of a preferred adhesive is provided merely by way of illustration and not of limitation.

Figure 18:
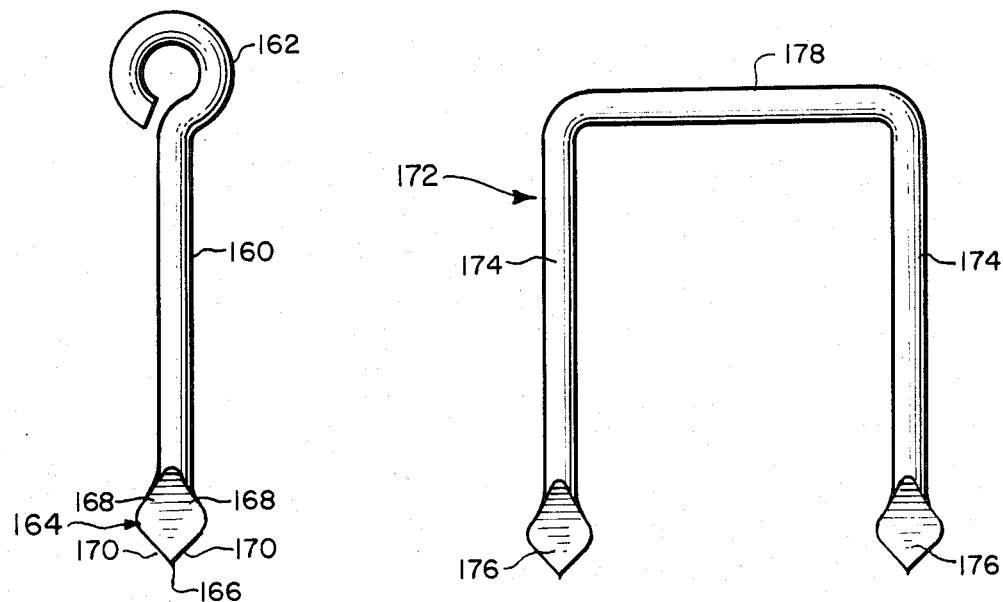
FIG. 18 is an enlarged view of an alternative embodiment of a pin suitable for use in the device of FIG. 10.
Figure 19:
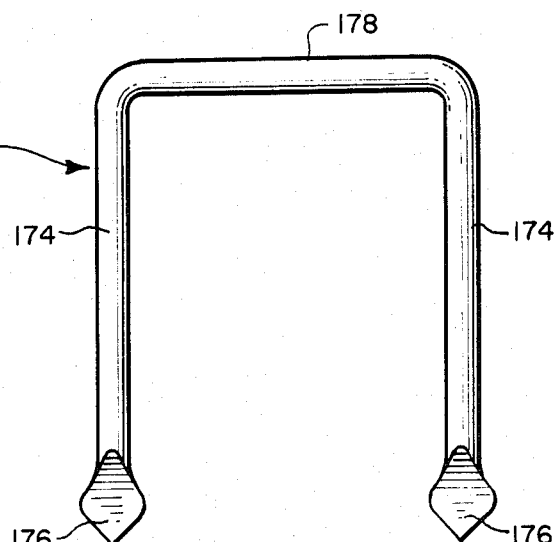
FIG. 19 is an enlarged view of a second alternative embodiment of a pin suitable for use in the device of FIG. 10 or the device of FIG. 20.

As shown in FIG. 10, the skin closure device 100 also includes two sets of pins 150. Each of these pins 150 is provided with an enlarged head 152 as well as with a point 154 which defines a knife-like cutting edge 156. The nature of the points 154 is best shown in FIGS. 18 and 19, which disclose two alternate embodiments of the pin 150. In FIG. 18, the pin 160 is provided with a looped end section 162 and a point 164 which defines an apex 166. In addition, the point 164 defines two enlarged shoulders 168, and a knife-like cutting edge 170 which extends along the sides of the shoulders 168 to the apex 166.

The pin shown in FIG. 19 is yet another alternative embodiment 172 which includes two pin shafts 174, each of which defines a respective point 176 of the type described above. A pin shank 178 connects the two shafts 174 together such that the two shafts 174 form a unit. This embodiment 172 provides the advantage of rapid pin insertion and removal. Simple finger pressure is sufficient to insert the pin 172 easily due to the area and spacing of the shank 178. In each of the pins 150, 160, 172, the angle defined by the cutting edges 156, 170 is preferably about 60 degrees.

By way of example only, the pins can be made of type 316 stainless steel. Of course, other metals or plastic materials of suitable mechanical properties can be substituted. Merely by way of example, in the preferred embodiments discussed above, the shaft of each of the pins is about 0.021 inches in diameter, and the diameter of the pin guides is about 0.0212 inches in diameter. These dimensions provide a close fit of the pins in the pin guides in order to orient the pins properly. In each case, both the heads 152, 162, 178 and the points 154, 164, 176 of the pins are enlarged so as to prevent the pins from escaping from the pin guides 122. In this way, each pin is slidably captured within its pin guide and cannot readily be lost or removed from the pin harness. In this preferred embodiment, the presently preferred length of the pin 150 from the tip of the point 154 to the underside of the head 152 is about 0.311 inches. An alternative embodiment provides a pin 150 with a length of about 0.230 inches.

Figure 14:
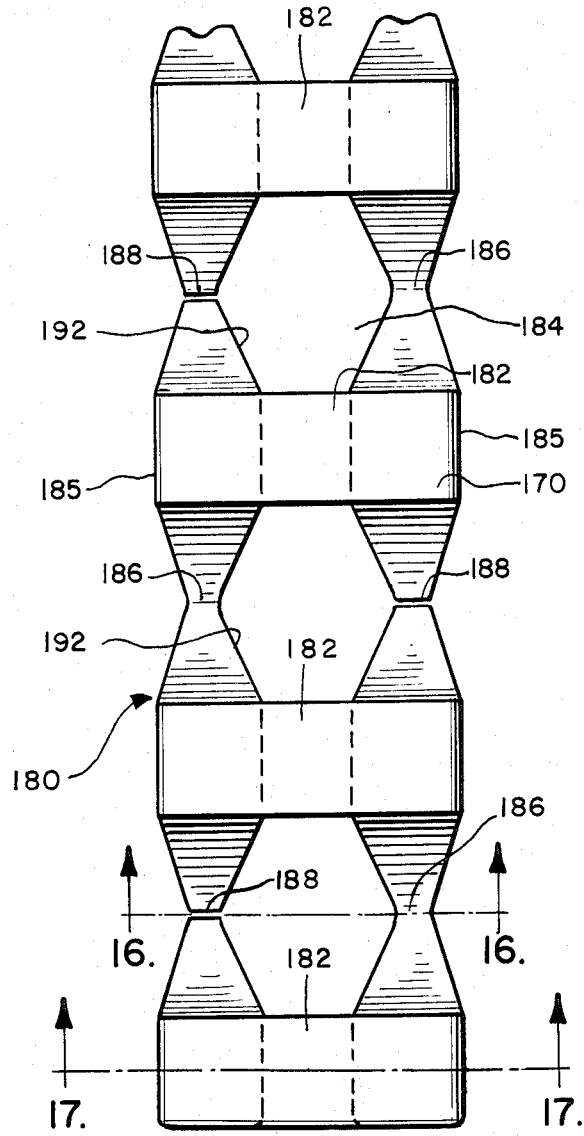
FIG. 14 is a top plan view of a portion of the housing of the embodiment of FIG. 10.
Figure 15:
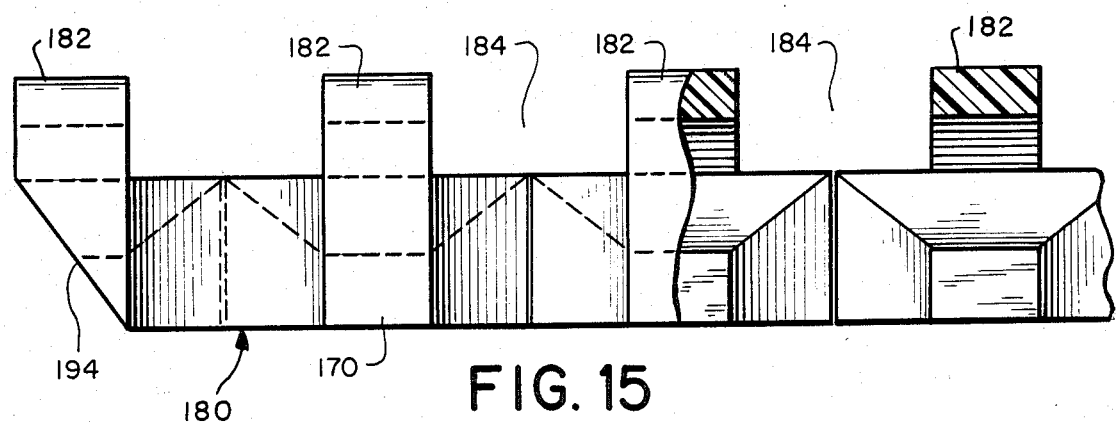
FIG. 15 is a side elevational view of a portion of the housing of FIG. 14.
Figure 16:
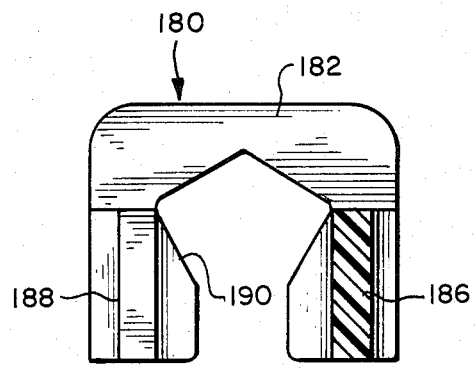
FIG. 16 is a sectional view taken along line 16—16 of FIG. 14.
Figure 17:
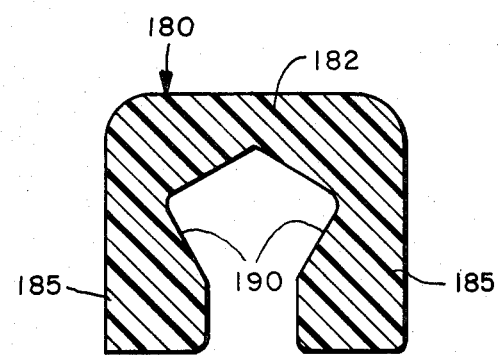
FIG. 17 is a sectional view taken along line 17—17 of FIG. 14.

Turning now to FIGS. 14 through 16, the skin closure device 100 also includes a housing 180. This housing 180 is an elongated member which defines a U-shaped cross section. The housing 180 is made up of a plurality of bridge sections 182 which interconnect two opposed side skirts or sidewalls 185. An array of cross slots 184 are positioned between the bridge portions 182 to intersect the channel 190 defined between the sidewalls 185. These cross slots 184 provide openings or apertures 192 which facilitate the drainage of fluids from the skin wound. As best shown in FIG. 14, each of the sidewalls 185 defines alternately positioned narrowed regions 186 and severed regions 188. When the housing 180 is bent laterally in the plane of FIG. 14, the severed regions 188 open and the narrowed regions 186 bend to allow the entire housing 180 to bend laterally. Preferably, the housing 180 is substantially more rigid to bending in a plane perpendicular to the plane of FIG. 14 than in the plane of FIG. 14. Preferably, both ends 194 of the housing 180 are beveled to facilitate assembly of the skin closure device.

In the preferred embodiment 100 of FIGS. 10 through 19, the pin harnesses 110 and the housing 180 are preferably formed of a high density ethylene hexene-1 copolymer such as the material marketed by Phillips Chemical Company, Battlesfield, Okla. as Marlex type HHM 5502. This material has been found to provide excellent properties in terms of minimum skin reaction and optimum rigidity. The flexibility of this material is temperature dependent, and it has been found to be suitably rigid when the skin closure device 100 is being installed adjacent the skin wound and yet to conform properly to the contour of the skin wound as the skin closure device warms to skin temperature. Preferably, the pin harnesses 110 and the housing 180 are injection-molded and the pin guides 122 are cored. It should be understood that it is not essential in all preferred embodiments that the pin guides 122 be circular in cross section; square pin guides or pin guides of other cross-sectional shape can be substituted. The severed regions 188 in the housing 180 can be formed either by injection molding or by a cutting operation subsequent to injection molding.

The pins 150 of the preferred embodiment described above are preferably first formed with a cold forged head and a standard conical point, and are then assembled in the respective pin guides 122. The point 154 which defines the cutting edges 156 is then formed in a three-step cold forging operation. The first step is a cutting step to trim off the pin at the desired length. This cutting operation is performed in a first station of a suitable metal forming machine. The second step is to coin the points at a second station of the metal forming machine to a paddle shape having a thickness in the range of about 0.002 inches to about 0.007 inches. Then, the point 154 is cut in a third station to a suitable diamond shape. This cutting operation creates the cutting edges 156. By the process described above, the points 154 can be formed in the pins 150 only after the pins 150 have been inserted in the pin guides 122. In this way, the pins 150 are captured securely within the pin guides 122. Preferably, the stainless steel from which the pins 150 are formed is work hardened to a tensile strength of between 210,000 and 230,000 psi.

Preferably, the skin closure device 100 (including the pin harnesses 110, the adhesive layer 140, the pins 150, and the housing 180) is packaged in a suitable material along with a pin-pushing device formed of Marlex as described above and defining a recessed end sized to fit over the heads 152 of the pins 150. Of course, other types of pin pushing devices, such as forceps-like devices adapted to insert a number of pins at once, can also be used.

These packages also preferably include a quantity of a suitable adhesive. In the preferred embodiment, this adhesive is contained in a glass bottle having a permeable neoprene applicator. In the presently preferred embodiment, an adhesive of the type described above is used. However, in order to provide reduced drying times, the Type 355 Dow Corning adhesive is allowed partially to evaporate before the glass bottle is sealed. In the presently preferred embodiment, 11 cc of Type 355 adhesive is allowed to evaporate down to about 6 cc before the bottle is sealed.

Once the package has been assembled in a clean room in accordance with the regulations of 21 CFR820, it is then preferably sterilized. This can be done by placing a large number of the packages near a Cobalt 60 source of gamma radiation. Preferably, the packages are rotated within a radiation chamber until a dosage of at least 2.5 mega rads is obtained. In this way, the entire skin closure device along with its adhesive is completely sterilized.

The skin closure device 100 described above in conjunction with FIGS. 10 through 19 can be used in the manner of the preferred embodiment of FIGS. 5 to 9a. Preferably, adhesive from the applicator is applied to the skin on both sides of the skin wound. Then the skin contacting surfaces 124 of the pin harness 110 are adhesively bonded to the skin in the desired position and the pins 150 are then pushed into the skin. Preferably, the epidermis is adhesively secured to the pin harnesses at points closely adjacent to the marginal edge of the skin wound. In order to obtain optimum results, this region of adhesive bonding should extend to within 0.5 millimeters of the skin wound.

As described above, the skin closure device 100 can either be applied to unbroken skin prior to the formation of a surgical incision, or alternately it can be applied to the marginal edges of the skin wound after the skin wound has been formed. In either case, the housing 180 is used to approximate the rails 116 of the pin harnesses 110 in order to close the skin wound quickly, efficiently and precisely. Generally, no occlusive dressing is needed.

The preferred embodiment 100 described above provides a number of important advantages. Since the skin contacting surfaces 124 are bonded by the adhesive layer 140 to the epithelium at points closely adjacent to the marginal edge of the skin wound, the skin contacting members 112 serve to bring together and align the epithelium layers precisely. Furthermore, the pins 150 are dimensioned such that the points 154 mechanically engage the dermis. The broad surfaces of the points 154 serve to enhance this mechanical engagement. When the housing 180 is used to bring the points 154 of the pins 150 together, the pins 150 serve to mechanically engage the dermis and to cause the marginal edges of the dermis adjacent the wound to come together in proper alignment. In this way, the skin closure device 100 serves automatically and reliably to align both the epithelium layer and the dermis in precise, edge-to-edge contact and alignment. In this way, healing of the skin wound is facilitated and the formation of scar tissue at the skin wound is minimized.

Furthermore, the embodiment of FIGS. 10 through 19 provides pins 150 which are slidable with respect to the pin harnesses 110, yet which are securely captured in the pin guides 122. This structure allows individual pins 150 to be removed from the skin if desired, yet substantially prevents the loss of individual pins. If desired, recesses can be formed in the underside of the pin guides 122 to receive the pin points 154.

Yet another advantage of this invention is that the adhesive layer 140 extends adjacent to and around the pins 150. The adhesive layer 140 operates to immobilize the epithelium layer of the skin around the pins 150 in order to minimize relative motion therebetween. Such relative motion can result in the formation of undesirable scar tissue. The layer of adhesive 140 around the pins 150 further serves to seal the opening in the epithelium layer made by the pins 150 in order to reduce infection and the introduction of foreign material into the epithelium.

Figure 20:
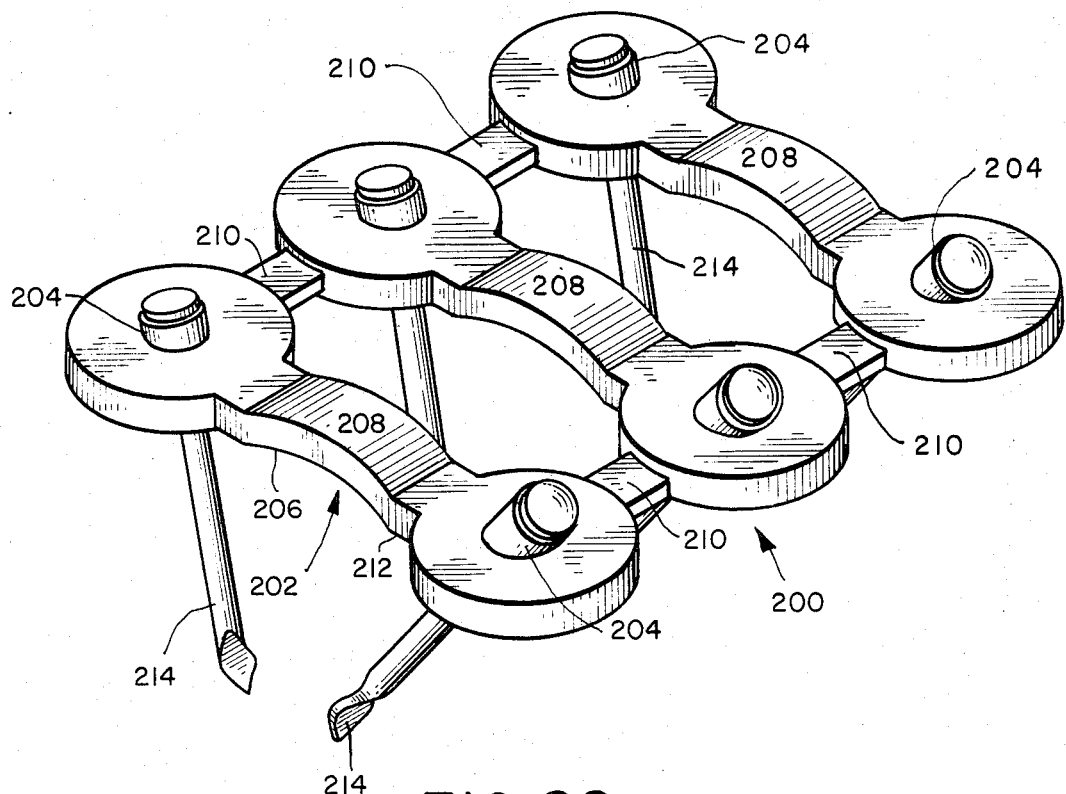
FIG. 20 is a perspective view of a third preferred embodiment of the skin closure device of this invention.

Turning now to FIG. 20, a third preferred embodiment of this invention comprises a plurality of staples 200. Each of the staples 200 is formed of a bridge member 202 which defines two opposed pin guides 204 and an intermediate portion 208 which interconnects the pin guides 204. The underside of the pin guides 204 and the intermediate portion 208 defines a skin contacting surface 206. Adjacent staples 200 are interconnected by means of two side strips 210 which can easily be severed as desired. A layer of a suitable skin adhesive 212 is provided on the entire skin contacting surface 206 (including the underside of the bridge member 202) to form a secure bond between the skin contacting surface 206 and the epithelium on either side of a skin wound. Two pins 214 are captured in and guided by respective ones of the pin guides 204. In general, the details of construction with regard to materials and the shapes of the pins 214 are similar to those described above in conjunction with the skin closure device 100.

The staple 200 is used by first severing the side strips 210 as desired to obtain the desired number of adjacent staples 200. Then the skin contacting surface 206 is adhesively bonded to the skin to bridge a skin wound, using adhesive techniques similar to those described above in conjunction with the skin closure device 100. Then the pins 214 are pushed into the skin, guided by the pin guides 204.

The staple 200 does not provide the advantages of the two preferred embodiments described above with regard to speed of wound closure. However, this embodiment of the invention does provide many of the advantages described above in conjunction with the skin closure device 100. For example, the staple 200 combines the use of an adhesive layer 212 immediately adjacent the marginal edge of the epithelium layer at the skin wound with pins 214 positioned to mechanically engage the dermis adjacent the skin wound in order to bring these two important skin layers together in proper alignment to facilitate healing of the skin wound and to minimize scar formation. This embodiment also provides the advantages described above with regard to the captured pins, the use of adhesive at the pin sites to immobilize the epithelium adjacent the pins, and the use of spade-shaped pin points to improve mechanical engagement between the pins and the dermis.

Figure 21:
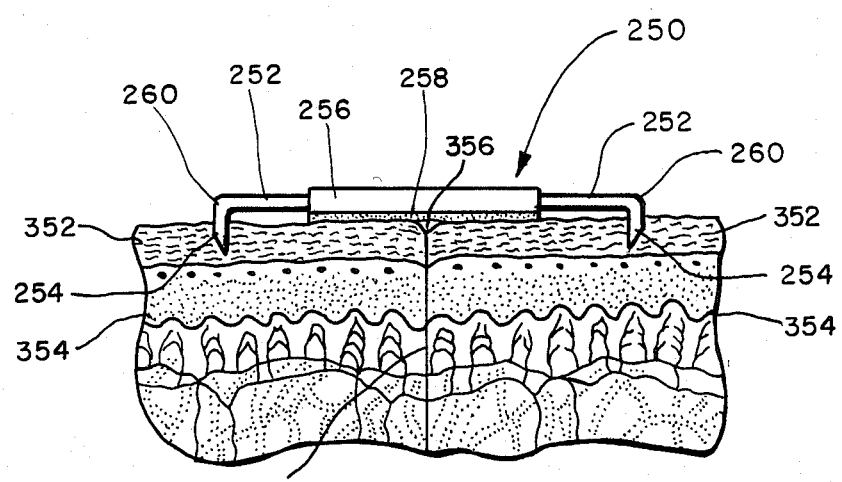
FIG. 21 is a sectional view of a fourth preferred embodiment of the skin closure device of this invention during an initial stage of insertion across a wound.
Figure 22:
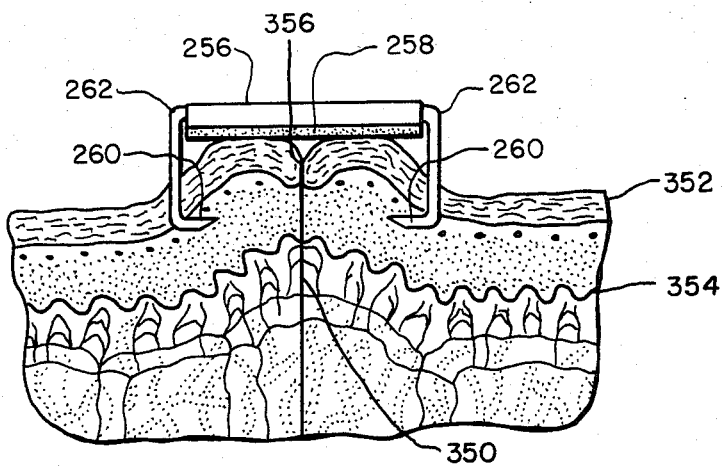
FIG. 22 is a sectional view of the embodiment of FIG. 21 as fully inserted.

Turning now to FIGS. 21 and 22, a fourth preferred embodiment of this invention comprises a staple 250 which includes two opposed staple members 252, each of which defines a respective point 254. These two staple members 254 protrude from opposite sides of a rigid staple bridge 256 which interconnects the two staple members 252. The underside of the staple bridge 256 is provided with an adhesive layer 258 of the type described above. Prior to insertion of the staple 250, each of the staple members 252 is provided with a first bend 260. During insertion, the skin is everted, and second bends 262 are formed in the two staple members 252 to configure the staple 250 as shown in FIG. 22. In this configuration, the staple members 252 mechanically engage the dermis in order to align the marginal edges of the dermis on opposed sides of the skin wound with one another and to hold them together. Furthermore, the adhesive layer 258 on the staple bridge 256 engages, aligns and holds together the marginal edges of the epithelium adjacent the skin wound. In this way, both the epithelium and the dermis layers are properly aligned and held together to facilitate healing and to reduce the formation of scar tissue. In many applications, the staple 250 provides reduced precision of alignment of skin layers as compared to the preferred embodiments described above.

Figure 23:
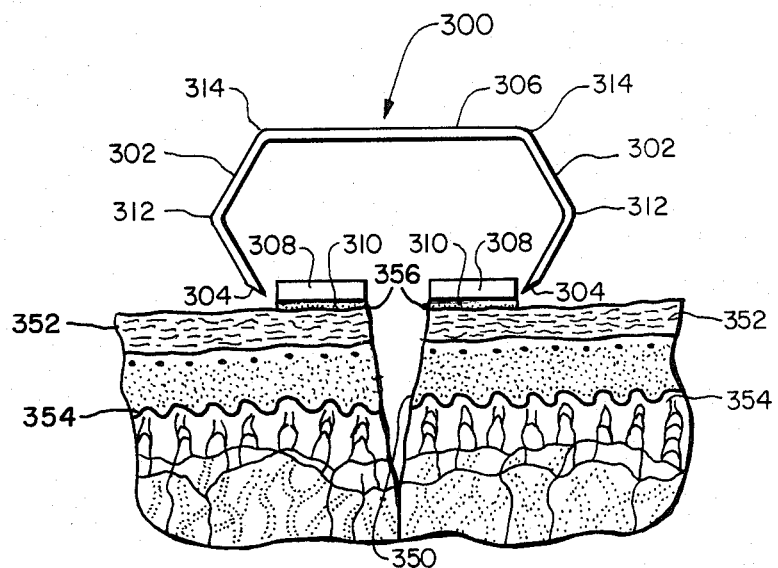
FIG. 23 is a sectional view of a fifth preferred embodiment of the skin closure device of this invention during an initial stage of insertion across a wound.
Figure 24:
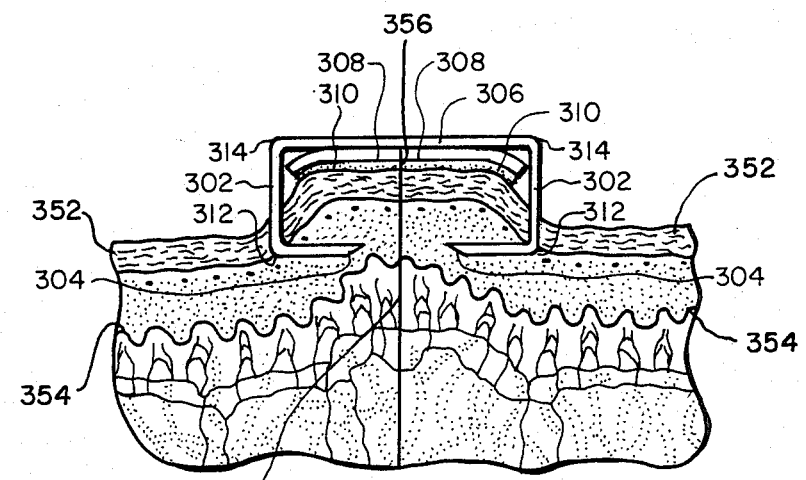
FIG. 24 is a sectional view of the embodiment of FIG. 23 as fully inserted.

Turning now to FIGS. 23 and 24, a fifth preferred embodiment of the skin closure device of this invention comprises a staple 300. The staple 300 is made up of two opposed staple members 302, each of which defines a respective staple point 304. The two staple members 302 are integrally formed with and interconnected by a rigid staple bridge 306. Two adhesive members 308 are each provided with an adhesive layer 310 of the type described above. In use, the two adhesive members 308 are first adhesively bonded to the marginal edges of the epithelium adjacent the skin wound. The staple members 302 are each provided with first and second bends 312 and 314. Then the staple members 302 are forced into the skin and the second bend 314 is made more acute until the staple bridge 306 captures the adhesive members 308 against the epithelium. In this preferred embodiment, the staple members 302 cooperate with the adhesive members 308 to force the adhesive members 308 together. In a manner similar to that of the staple 250 of FIGS. 21 and 22, the staple members 302 mechanically engage the dermis and the adhesive members 308 adhesively engage the epidermis at points closely adjacent to the marginal edges of the skin wound. In this way, both the epidermis and the dermis layers on either side of the skin wound are properly aligned and held together in order to facilitate healing and to minimize the formation of scar tissue.

From the foregoing, it should be apparent that a variety of skin closure devices have been disclosed which operate to align and approximate both superficial and internal layers of the skin in order to minimize the formation of scar tissue. Of course, a wide variety of changes and modifications to the preferred embodiments described above will be apparent to those skilled in the art. For example, the housing 180 can be replaced with a clamp such as a spring clamp, or it can be designed to snap on and off of the pin harnesses 110. Materials, dimensions, proportions, and shapes can all be modified as desired for individual applications. For example, elements such as the pin harnesses 110 and the housing 180 can be formed of aluminum or stainless steel. It is therefore intended that the foregoing detailed description be regarded as illustrative rather than limiting, and that it be understood that it is the following claims, including all equivalents, which are intended to define the scope of this invention.

I claim:

1. A closure device for a skin wound which defines two marginal edges, each of which comprises a superficial skin layer and an internal skin layer, said device comprising:

means for defining first and second surfaces adapted to be positioned at respective sides of the skin wound;

pin means for mechanically engaging the two internal skin layers near the two marginal edges of the wound to respective ones of the first and second surfaces;

adhesive means for adhesively bonding exterior surfaces of the two superficial skin layers closely adjacent to the two marginal edges of the wound to respective ones of the first and second surfaces, said adhesive means extending between the first and second surfaces and the superficial skin layer into a region between the pins and the marginal edges of the wound; and means, coupled to the first and second surfaces, for positioning the first and second surfaces to hold the two superficial skin layers together in alignment, and for simultaneously positioning the pin means to hold the two internal skin layers together in alignment, in order to promote rapid healing of the skin wound and to minimize the formation of scar tissue;

said pin means and said first and second surfaces configured to allow the first and second surfaces to be adhesively bonded to the exterior surafces of the two superficial skin layers prior to engagement of the pin means with the internal skin layers.

2. The invention of claim 1 wherein the first surface comprises a first pin harness adapted to be bonded to one of the two marginal edges by the adhesive means and supporting a first plurality of pins included in the pin means; wherein the second surface comprises a second pin harness adapted to be bonded to the other of the two marginal edges by the adhesive means and supporting a second plurality of pins included in the pin means; and wherein the positioning means comprises means for releasably securing the first pin harness to the second pin harness and for limiting movement therebetween normal to the superficial skin layer.

3. The invention of claim 2 wherein the securing means comprises a housing shaped to fit over and clamp together portions of the first and second pin harnesses.

4. The invention of claim 1 wherein the first and second surfaces and the positioning means comprise a bridge member which extends across the skin wound, which is bonded to the two superficial layers by the adhesive means, and which is secured to the two internal layers by the pin means.

5. The invention of claim 4 wherein the pin means comprises at least two staple members, each of which extends from a respective side of the bridge member.

6. The invention of claim 1 wherein the pin means comprises at least two staple members and wherein the positioning means comprises a staple bridge, connected between the two staple members over the adhesive means in order to capture the first and second surfaces and the adhesive means in place over the skin wound.

7. The invention of claim 1 wherein the adhesive means is shaped to adhesively bond the two superficial skin layers at regions which extend to within 0.5 mm of the two marginal edges of the skin wound.

8. A device for use in the rapid closure of skin wounds, comprising:

(a) a pair of strips of semi-rigid material for positioning one immediately along either side of a wound to be closed, the strips having respective skin-contacting first portions which in use extend laterally away from the wound in mutually opposite directions and respective upstanding second portions which are integral with the respective first portions and which in use abut against one another over the wound;

(b) a layer of adhesive on the skin-contacting surface of the first portion of each strip for adherence of the strips to the skin, the adhesive layer positioned to extend to closely adjacent the skin wound into a region between the pins and the skin wound;

(c) a plurality of pins located along the length of the first portion of each strip and laterally spaced from the respective second portions of the strip, each pin being slidable relative to the first portion so as to permit the pin to be pushed downwardly into the skin, after the skin-contacting surfaces of the first portion of the respective strip have been adhered to the skin, from an initial position wherein the pin does not penetrate the skin to a holding position wherein the pin extends into the skin; and (d) an elongated housing adapted to engage and hold together in abutting relationship the upstanding second portion of the strips and to limit relative vertical movement therebetween.

9. A device for use in the rapid closure of skin wounds, comprising:

(a) a pair of strips of semi-rigid material for positioning one immediately along either side of a wound to be closed, the strips having respective skin-contacting first portions which in use extend laterally away from the wound in mutually opposite directions and respective upstanding second portions which are integral with the respective first portions and which in use abut against one another over the wound;

(b) a plurality of pins located along the length of the first portion of each strip and laterally spaced from the respective second portion of the strip, each pin being slidable relative to the first portion so as to permit the pin to be pushed downwardly into the skin from an initial position wherein the pin does not penetrate the skin;

(c) a layer of adhesive on the skin-contacting surface of the first portion of each strip for adherence of the strips to the skin;

(d) an elongated housing adapted to engage and hold together in abutting relationship the upstanding second portions of the strips and to limit relative vertical movement therebetween; and (e) means for defining a plurality of apertures along the length of each strip at least in the region of the junction of the first and second portions to provide wound drainage sites.

10. The invention of claim 8, wherein the skin-contacting first portion of each strip comprises a plurality of lateral fingers spaced apart along the length of the strip and joined at their inner ends to the upstanding second portion of the strip.

11. The invention of claim 10, wherein in each strip the spaces between the fingers extend partially upwardly into the respective upstanding second portion to provide a plurality of drainage sites.

12. The invention of claim 10, wherein each strip the pins are located adjacent the ends of the fingers remote from the respective upstanding second portion.

13. The invention of claim 8, wherein the abutting upstanding second portions are spaced apart at their lower regions to define a gap immediately above the wound to permit eversion of the skin during healing.

14. The invention of claim 13, wherein in each strip the skin-contacting surface of the first portion is joined by a smooth upwardly curved surface to the surface of the second portion which abuts the corresponding surface of the other strip, the two curved surfaces defining the gap.

15. The invention of claim 8, wherein the pins have enlarged heads to prevent their movement fully through the first portion of the respective strip.

16. The invention of claim 8, wherein the pins have a knife-like tapered portion at the end thereof to be inserted into the skin.

17. The invention of claim 8, wherein the housing is slidable along the length of the strips from one end to engage the upstanding second portions.

18. The invention of claim 17 wherein the housing is of generally U-shaped cross-section with a top bridge portion and downwardly extending skirt portions on either side which in use embrace the upstanding abutting second portions of the strips.

19. A device for use in the rapid closure of skin wounds, comprising:
(a) a pair of strips of semi-rigid material for positioning one immediately along either side of a wound to be closed, the strips having respective skin-contacting first portions which in use extend laterally away from the wound in mutually opposite directions and respective upstanding second portions which are integral with the respective first portions and which in use abut against one another over the wound;
(b) a plurality of pins located along the length of the first portion of each strip and laterally spaced from the respective second portion of the strip, each pin being slidable relative to the first portion so as to permit the pin to be pushed downwardly into the skin from an initial position wherein the pin does not penetrate the skin;
(c) a layer of adhesive on the skin-contacting surface of the first portion of each strip for adherence of the strips to the skin; and
(d) an elongated housing adapted to engage and hold together in abutting relationship the upstanding second portions of the strips and to limit relative vertical movement therebetween, said housing being of generally U-shaped cross section with a top bridge portion and downwardly extending skirt portions on either side which in use embrace the upstanding abutting second portions of the strips, said bridge portion of the housing being apertured along its length.

20. A device for use in the rapid closure of skin wounds, corprising:
(a) a pair of strips of semi-rigid material for positioning one immediately along either side of a wound to be closed, the strips having respective skin-contacting first portions which in use extend laterally away from the wound in mutually opposite directions and respective upstanding second prtions which are integral with the respective first portions and which in use abut against one another over the wound;
(b) a plurality of pins located along the length of the first portion of each strip and laterally spaced from the respective second portions of the strip, each pin being slidable relative to the first portion so as to permit the pin to be pushed downwardly into the skin from an initial position wherein the pin does not penetrate the skin;
(c) a layer of adhesive on the skin-contacting surface of the first portion of each strip for adherence of the strips to the skin; and
(d) an elongated housing adapted to engage and hold together in abutting relationship the upstanding second portions of the strips and to limit relative vertical movement therebetween;
said pins having a knife-like tapered portion at the end thereof to be inserted into the skin, each of said knife-like tapered portions being shaped to prevent the tapered porrtion from moving through the first portion of the respective strip, thereby capturing the pins in the respective strips.

21. The invention of claim 8, wherein the layer of adhesive is also positioned to extend to closely adjacent the pin locations.

22. The invention of claim 8 wherein the layer of adhesive is positioned to extend to within 0.5 mm of the skin wound.

23. A skin closure device for a skin wound which defines two marginal edges, each of which comprises a respective superficial skin layer and a respective internal skin layer, said device comprising:
first and second pin harnesses, each of which defines a plurality of skin contacting members, each of which defines a respective pin guide, said skin contacting members defining skin contacting surfaces shaped to contact the respective superficial skin layers at points closely adjacent the respective marginal edges;
first and second adhesive layers of a skin adhesive bonded to the skin contacting surfaces of the first and second pin harnesses, respectively, in order to bond said skin contacting surfaces to the respective superficial skin layers at said points closely adjacent the respective marginal edges;
first and second sets of pins, each set mounted in the pin guides of a respective one of the pin harnesses such that the pins are slidable in the respective pin guides, each of said pins defining an enlarged head and an enlarged knife-like point, each of which is too large to move through the respective pin guide such that each of the pins is captured in the respective pin guide, each of said pins having a length adapted to allow the pin to engage the respective internal layer; and
means for holding the first and second pin harnesses together in alignment such that in use the adhesive layer maintains the two superficial layers together in alignment and the pins maintain the two internal layers together in alignment in order to promote rapid healing of the skin wound and to minimize scar formation.

24. The invention of claim 23 wherein the holding means comprises a housing shaped to fit over and clamp together portions of the first and second pin harnesses.

25. The invention of claim 24 wherein the housing defines a central channel and an array of spaced cross slots which intersect the channel to promote drainage from the skin wound between the pin harnesses.

26. The invention of claim 25 wherein the housing defines a pair of sidewalls, one on either side of the channel, and wherein each sidewall defines an array of alternating narrowed regions and severed regions to promote lateral flexibility of the housing.

27. The invention of claim 23 wherein each of the pin harnesses defines a rail positioned above the respective skin contacting surface, and wherein each of the skin contacting members defines a first member, which defines the respective skin contacting surface, and a second member, secured between the first member and the rail, said rail, first members, and second members cooperating to promote drainage from the skin wound between the skin contacting members.

28. The invention of claim 23 wherein the adhesive layers extend closely adjacent to the pin guides to seal the superficial layers around the pins and to immobilize the superficial layers adjacent to the pins with respect to the pins and the pin harnesses.

29. The invention of claim 23 wherein the adhesive layers are positioned to bond the skin contacting surfaces to the superficial skin layers to within 0.5 mm of the respective marginal edges.

30. The invention of claim 1 wherein the pin means are slidable in the first and second surfaces.

31. A closure device for a skin wound which defines two marginal edges, each of which comprises a superficial skin layer and an internal skin layer, said device comprising:
means for defining first and second surfaces adapted to be positioned at respective sides of the skin wound;
pin means for mechanically engaging the two internal skin layers near the two marginal edges of the wound to respective ones of the first and second surfaces;
adhesive means for adhesively bonding exterior surfaces of the two superficial skin layers closely adjacent to the two marginal edges of the wound to respective ones of the first and second surfaces, said adhesive means extending between the first and second surfaces and the superficial skin layer into a region between the pins and the marginal edges of the wound; and
means, coupled to the first and second surfaces, for positioning the first and second surfaces to hold the two superficial skin layers together in alignment, and for simultaneously positioning the pin means to hold the two internal skin layers together in alignment, in order to promote rapid healing of the skin wound and to minimize the formation of scar tissue;
said positioning means comprising:
a first pin harness adapted to be bonded to one of the two marginal edges by the adhesive means and supporting a first plurality of pins included in the pin means;
a second pin harness adapted to be bonded to the other of the two marginal edges by the adhesive means and supporting a second plurality of pins included in the pin means; and
means for releasably securing the first pin harness to the second pin harness and for limiting movement therebetween normal to the superficial skin layer;
said securing means comprising a housing shaped to fit over and clamp together portions of the first and second pin harnesses; said housing defining a plurality of drainage apertures along its length.

32. A closure device for a skin wound which defines two marginal edges, each of which comprises a superficial skin layer and an internal skin layer, said device comprising:
means for defining first and second surfaces adapted to be positioned at respective sides of the skin wound;
pin means for mechanically engaging the two internal skin layers near the two marginal edges of the wound to respective ones of the first and second surfaces;
adhesive means for adhesively bonding exterior surfaces of the two superficial skin layers closely adjacent to the two marginal edges of the wound to respective ones of the first and second surfaces, said adhesive means extending between the first and second surfaces and the superficial skin layer into a region between the pins and the marginal edges of the wound; and
means, coupled to the first and second surfaces, for positioning the first and second surfaces to hold the two superficial skin layers together in alignment, and for simultaneously positioning the pin means to hold the two internal skin layers together in alignment, in order to promote rapid healing of the skin wound and to minimize the formation of scar tissue;
said positioning means comprising:
a first pin harness adapted to be bonded to one of the two marginal edges by the adhesive means and supporting a first plurality of pins included in the pin means;
a second pin harness adapted to be bonded to the other of the two marginal edges by the adhesive means and supporting a second plurality of pins included in the pin means; and
means for releasably securing the first pin harness to the second pin harness and for limiting movement therebetween normal to the superficial skin layer;
each of said pins defining an enlarged head and an enlarged point, such that each of the pins is slidable in the respective pin harness and positively captured in place.

33. A closure device for a skin wound which defines two marginal edges, each of which comprises a superficial skin layer and an internal skin layer, said device comprising:
means for defining first and second surfaces adapted to be positioned at respective sides of the skin wound;
pin means for mechanically engaging the two internal skin layers near the two marginal edges of the wound to respective ones of the first and second surfaces;
adhesive means for adhesively bonding exterior surfaces of the two superficial skin layers closely adjacent to the two marginal edges of the wound to respective ones of the first and second surfaces, said adhesive means extending between the first and second surfaces and the superficial skin layer into a region between the pins and the marginal edges of the wound; and means, coupled to the first and second surfaces, for positioning the first and second surfaces to hold the two superficial skin layers together in alignement, end for simultaneously positioning the pin means to hold the two internal skin layers together in alignment, in order to promote rapid healing of the skin wound and to minimize the formation of scar tissue;

said positioning means comprising:

a first pin harness adapted to be bonded to one of the two marginal edges by the adhesive means and supporting a first plurality of pins included in the pin means;

a second pin harness adapted to be bonded to the other of the two marginal edges by the adhesive means and supporting a second plurality of pins included in the pin means; and means for releasably securing the first pin harness to the second pin harness and for limiting movement therebetween normal to the superficial skin layer;

said first and second pin harness each defining a respective array of fingers adapted to contact the superficial skin layer, adjacent fingers being separated by gaps which extend to the respective marginal edges to allow drainage from the skin wound.

34. The invention of claim 3 wherein the housing is of generally U-shaped cross section with a top bridge portion extending between spaced skirt portions, and wherein the skirt portions define axially spaced hinge portions of increased flexibility.

35. The invention of claim 34 wherein the skirt portions also define a plurality of axially spaced slits interspersed among the hinge portions.

36. A closure device for a skin wound which defines two marginal edges, each of which comprises a superficial skin layer and an internal skin layer, said device comprising:

means for defining first and second surfaces adapted to be positioned at respective sides of the skin wound;

pin means for mechanically engaging the two internal skin layers near the two marginal edges of the wound to respective ones of the first and second surfaces;

adhesive means for adhesively bonding exterior surfaces of the two superficial skin layers closely adjacent to the two marginal edges of the wound to respective ones of the first and second surfaces, said adhesive means extending between the first and second surfaces and the superficial skin layer into a region between the pins and the marginal edges of the wound; and means, coupled to the first and second surfaces, for positioning the first and second surfaces to hold the two superficial skin layers together in alignment, and for simultaneously positioning the pin means to hold the two internal skin layers together in alignment, in order to promote rapid healing of the skin wound and to minimize the formation of scar tissue;

said positioning means comprising a bridge member which extends across the skin wound, which bridge member is bonded to the two superficial layers by the adhesive means and is secured to the two internal layers by the pin means;

said bridge member defining at least two pin guides and said pin means comprising at least two pins, each mounted to slide in a respective one of the pin guides.

* * * * *

UNITED STATES PATENT AND TRADEMARK OFFICE
CERTIFICATE OF CORRECTION

PATENT NO. : 4,526,173
DATED : July 2, 1985
INVENTOR(S) : Joseph C. M. Sheehan

It is certified that error appears in the above-identified patent and that said Letters Patent is hereby corrected as shown below:

IN THE CLAIMS

In Claim 1 (column 17, line 38), please delete "surafces" and substitute therefor --surfaces--;

In Claim 20 (column 19, line 66), please delete "corprising" and substitute therefor --comprising--;

In Claim 20 (column 20, line 4), please delete "prtions" and substitute therefor --portions--;

In Claim 20 (column 20, line 25), please delete "porrtion" and substitute therefor --portion--;

In Claim 33 (column 23, line 5), please delete "alignement" and substitute therefor --alignment--;

In Claim 33 (column 23, line 6), please delete "end" and substitute therefor --and--;

In Claim 33 (column 23, line 24, please delete "harness" and substitute therefor --harnesses--.

UNITED STATES PATENT AND TRADEMARK OFFICE
CERTIFICATE OF CORRECTION

PATENT NO. : 4,526,173

DATED : July 2, 1985

INVENTOR(S) : Joseph C. M. Sheehan

It is certified that error appears in the above-identified patent and that said Letters Patent is hereby corrected as shown below:

IN THE REFERENCES CITED
U.S. PATENT DOCUMENTS

In reference 3,863,640 2/1975, please correct the spelling of "Hauerstock" to --Haverstock--;

Please insert the following references:

| | | | |
|---|---|---|---|
| 2,523,812 | 4/1949 | Carr | 128/335 |
| 2,898,741 | 8/1953 | Milliken | |
| 3,516,409 | 6/1970 | Howell | 128/335 |
| 3,811,971 | 11/1971 | Scott | 128/335 |
| 3,933,158 | 1/1976 | Haverstock | 128/335 |
| 3,807,394 | 4/1974 | Attenborough | 128/92B |
| 3,831,608 | 8/1974 | Kletschka et al | 128/335 |
| 3,939,828 | 2/1976 | Mohr et al | 128/92B |
| 4,073,298 | 2/1978 | Le Roy | 128/337 |
| 4,114,624 | 9/1978 | Haverstock | 128/335 |

UNITED STATES PATENT AND TRADEMARK OFFICE
CERTIFICATE OF CORRECTION

PATENT NO. : 4,526,173
DATED : July 2, 1985
INVENTOR(S) : Joseph C. M. Sheehan

Page 3 of 3

It is certified that error appears in the above-identified patent and that said Letters Patent is hereby corrected as shown below:

IN A SECTION TO BE ENTITLED
"FOREIGN PATENT DOCUMENTS"

Please insert the following references:

2038038    Germany
    477704    Australia

Signed and Sealed this

Seventeenth Day of May, 1988

Attest:

DONALD J. QUIGG

Attesting Officer    Commissioner of Patents and Trademarks